United States Patent
Donaldson et al.

[19]

[11] Patent Number: 5,950,631
[45] Date of Patent: Sep. 14, 1999

[54] DEVICE AND METHOD FOR EQUALIZING THE PRESSURE IN THE MIDDLE EAR

[76] Inventors: John D. Donaldson; Krista M. Donaldson, both of 637 Lighthouse Way, Sanibel Island, Fla. 33957

[21] Appl. No.: 08/802,769

[22] Filed: Feb. 21, 1997

[51] Int. Cl.⁶ ............................. A61B 19/00; A61M 37/00
[52] U.S. Cl. ................................ 128/898; 604/26; 604/28
[58] Field of Search ........................ 604/26, 28; 128/898; 446/222

[56] References Cited

U.S. PATENT DOCUMENTS

| | | | |
|---|---|---|---|
| 816,106 | 3/1906 | Lindsay | 446/220 |
| 3,333,844 | 8/1967 | Jurschak | 446/220 |
| 4,749,377 | 6/1988 | Mendizabal . | |
| 4,817,626 | 4/1989 | Blaine . | |
| 5,419,762 | 5/1995 | Arick et al. . | |
| 5,431,636 | 7/1995 | Stangerup . | |
| 5,496,203 | 3/1996 | Murray | 446/220 |

*Primary Examiner*—David J. Isabella
*Attorney, Agent, or Firm*—Laura G. Barrow

[57] ABSTRACT

A method and device useful in assisting an individual in voluntarily inflating the middle ear is described, the device comprising (a) a body having a mouth portion and outer and inner surfaces defining a passageway communicating with an air orifice provided through the mouth portion; (b) a movable valve positioned within the passageway which divides the body into two inner compartments; and (c) a receptacle, such as a balloon, connected to a resistance port communicating through the body; whereby when the user blows air into the body through the mouth portion, the valve is opened to allow the air to enter one of the compartments to fill or inflate the receptacle, thus providing sustained pressure within the user's nasopharynx until substantial equilibrium of the middle ear at ambient pressure is achieved.

19 Claims, 10 Drawing Sheets

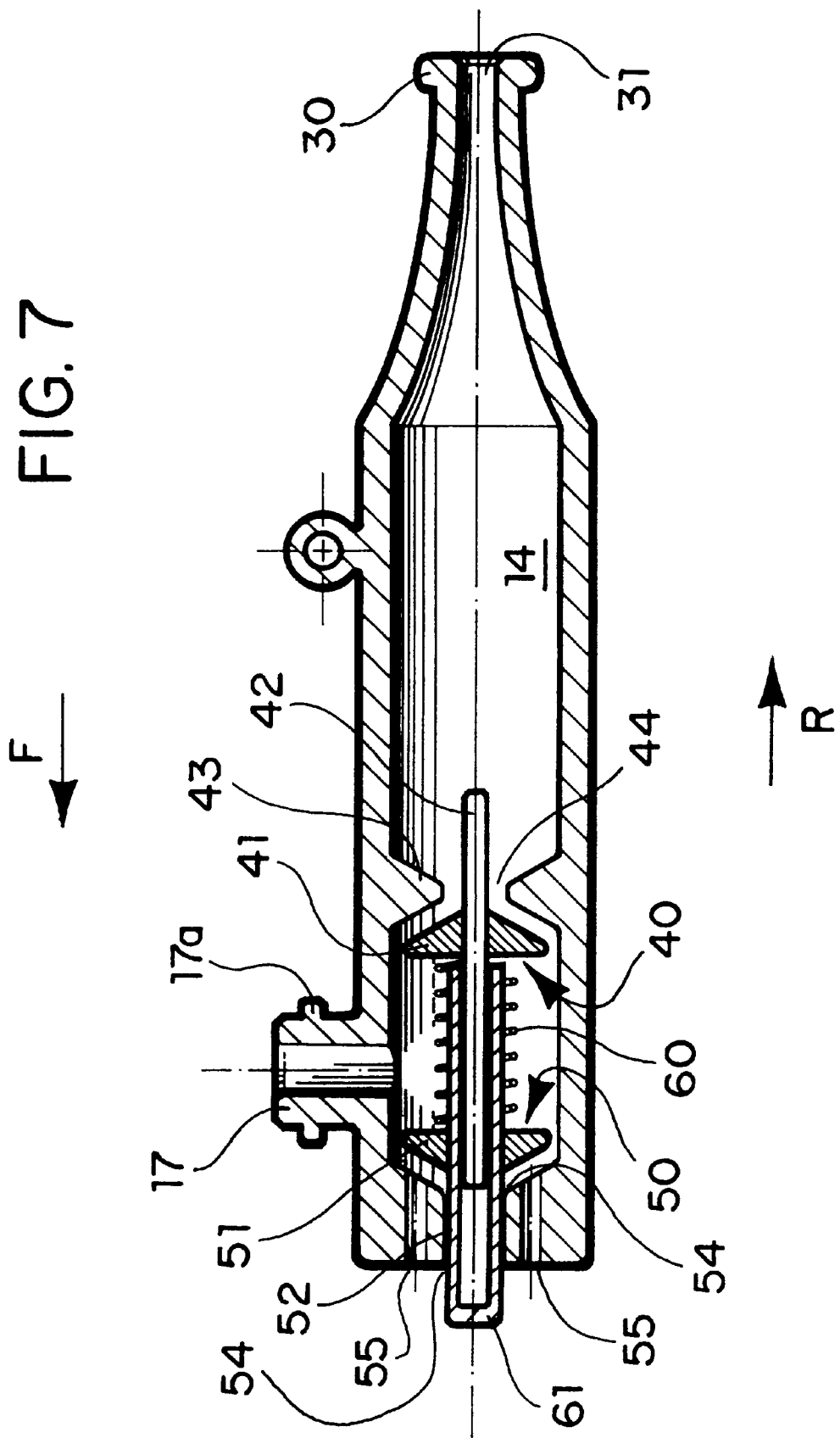

DEVICE AND METHOD FOR EQUALIZING THE PRESSURE IN THE MIDDLE EAR

BACKGROUND OF THE INVENTION

Aeration of the middle ear cleft is necessary to optimize hearing, to maintain tissue health and function, to prevent middle ear infection or fluid accumulation (OME), and to avoid pain when changing ambient external pressure. Significantly, many individuals, particularly children, are unable to electively move air from the nasopharynx to the middle ear.

The ear is divided into three anatomic and physiologic segments. The most lateral segment is the external ear, a skin lined passage extending from the exterior into the temporal bone of the skull, and terminating at the tympanic membrane.

The middle ear cleft is formed embryologically as an outpouching of the upper respiratory tract or nasopharynx within the temporal bone and communicates with the nasopharynx via the Eustachian tube. It consists of an air-filled cavity bounded laterally by the tympanic membrane and posteriorly by the mastoid cavity, an air reservoir with which it communicates through the antrum. The middle ear, or mesotympanum, contains three bones or ossicles connected in a chain between the tympanic membrane and the oval window, the lateral aspect of the cochlea or inner ear. The Eustachian tube is closed or collapsed in its resting state. Hearing is optimal when the middle ear is air-filled at ambient pressure.

The inner ear consists of the cochlea and the vestibular apparatus which are responsible for hearing and balance, respectively. These organs are connected directly to the central nervous system.

In the normal healthy individual, the air in the middle ear is maintained at the ambient pressure by insufflation though the Eustachian tube by momentary opening about every third time the individual swallows. No voluntary action is necessary to replenish air. This is necessary as the air and air components within the cleft are absorbed by the mucosal lining of the ear. Failure to renew the ambient pressure leads to various disease states.

A number disease conditions are observed that directly relate to abnormal Eustachian tube function. Almost all of these conditions relate to the individual's inability to open the normally closed tube either involuntarily or voluntarily to renew the middle ear ventilation, a state which may be acute (e.g. infection, allergy, etc.), chronic (anatomic abnormalities such as cleft palate or neurologic conditions) or developmental (e.g. immature physiology and inefficient musculature before skull base growth occurs). When the Eustachian tube ceases to function properly, the residual air in the middle ear is absorbed by the cavity lining (mucosa). This reduces the pressure in the middle ear below ambient (i.e. "negative pressure"), and disease may then be induced. The following are a few conditions that may result:

Otitis Media with Effusion: This is the most common pathological condition in children under two years of age. In the acute process, an upper respiratory infection in the nasopharynx hinders normal Eustachian tube function. Bacteria from this region migrate to the middle ear where fluid has been secreted in response to the negative pressure and an acute process is established resulting in the classic earache with fever and hearing loss. In chronic dysfunction, many complications can occur, including stretching of the eardrum, formation of pockets, cholesteatoma formation, hearing loss, and destruction of the ossicles or perforation of the tympanic membrane.

Barotrauma: The changing of the ambient pressure on the body requires pressure equalization into the middle ear cleft. Inability to equalize pressure results in pain on descent in commercial aircraft or upon diving into water, thus resulting in pain and possible rupture of the tympanic membrane.

The Eustachian tube can be opened voluntarily and the middle ear ventilated in most conditions by forcing air through it. This act requires a patent Eustachian tube and an intact neurologic system. Aeration of the middle ear may be accomplished with a relatively passive maneuver as simple as a yawn, but more force is generated by actively pushing air up the Eustachian tube by occluding the nose and mouth, followed by swallowing. Compression of the air in the pharynx by the squeeze of swallowing pushes air into the tube. Likewise, forcefully exhaling or blowing against a closed nose and mouth will achieve the same result. It is this concept that is assisted by the present invention without the use of an outside energy source, as discussed later in greater detail.

Before the turn of the century, Proetz described a method for physicians to inflate the middle ear. He described and popularized a system whereby a pressure was exerted in the anterior nostril while occluding the opposite side of the nose while the patient vocalized sounds known to close the posterior pharynx. Various forms of this inflation technique are utilized in clinical practice to this date. Patented devices such as those described in Blaine (U.S. Pat. No. 4,817,626), Arick et al. (U.S. Pat. No. 5,419,762), Mendizabal et al. (U.S. Pat. No. 4,749,377), and Strangerup (U.S. Patent No. 5,431,636) utilize one or more forms of the techniques described by Proetz in that they all exert a backward pressure to the Eustachian tube via the nostril and nose. In Arick et al. and Mendizabal, pressure is generated by a compressor powered by an electrical motor. In Strangerup and Elaine the pressure is generated by first closing one nostril and then blowing air through the other nostril into a balloon. All of these devices are fraught with the necessity of inserting a canula into the nose, often of an infected and less than cooperative individual. Nose bleeds often occur through the use of these devices, and the nasal end of the device is considered contaminated. Furthermore, utilization of these devices is normally limited to the privacy of a washroom.

In view of the problems with existing devices, it is therefore desirable to have a device that:

(1) requires only a single, easily performed action by an individual to increase the pressure in the nasopharynx for transmission to the ear via the Eustachian tube without the necessity of inserting any objects into the nasal cavity;

(2) permits variable and increasing pressure resistance for transmission to the nasopharynx depending upon individual user requirements; and (3) provides psychological and measurable incentives for children who would not otherwise cooperate in inflation of the middle ear.

SUMMARY OF THE INVENTION

The present invention is directed to a device and method for assisting in the inflation of a person's middle ear through the Eustachian tube, thereby resulting in pressure equalization in the middle ear. The simple and economical design and operation of the present invention, as discussed further below, is particularly useful during air travel, when frequent pressure equalization within the middle ear is necessary to prevent severe pain and possible rupture of the tympanic membrane.

In certain aspects of the present invention, the device comprises a body having a mouth portion and outer and inner surfaces, wherein the inner surface defines a passageway communicating with an air intake orifice provided within the mouth portion, the mouth portion being suitable for insertion into a user's mouth for blowing air through the passageway. The device further includes a valve that is movablely disposed within the passageway of the body to divide the passageway into two compartments, with the first compartment including the air intake orifice. The valve is further adapted to form a seal between the compartments at a resting state to prevent air from moving in retrograde direction between the compartments; however, when air is blown by the user into the body through the air intake orifice, the inflation valve is moved to an open position to allow passage of the air into the second compartment. Preferably, the device also includes a resistance port that is in communication with the second compartment and a receptacle, most preferably a balloon or other resistance device, that is attached to the resistance port. The combination valve and receptacle function to allow for the progressive increase in pressure required to open the valve by adding the continuous back pressure against the user. This has the effect of sustaining pressure within the nasopharynx to open the Eustachian tube, thereby equalizing the pressure within the middle ear. Provision of the balloon receptacle is preferred as an incentive device for children who would not otherwise use the device voluntarily. Other aspects of the invention include a second "deflation" valve housed within the second compartment and movably secured within the passageway to occlude an air outflow port communicating through the outer and inner surfaces of the body and into the second compartment. Actuation of the deflation valve allows for the removal of air from the body as well as any attached receptacle, thereby "deflating" the device. The device may also include a nose clip, preferably secured to the outer surface of the body, to occlude the nostrils anteriorly during use.

BRIEF DESCRIPTION OF THE DRAWINGS

FIG. 7 is a longitudinal cross-section taken along lines 7—7 of FIG. 6 illustrating both valves in an opened state.

DETAILED DESCRIPTION OF THE PREFERRED EMBODIMENTS

Figure 1:
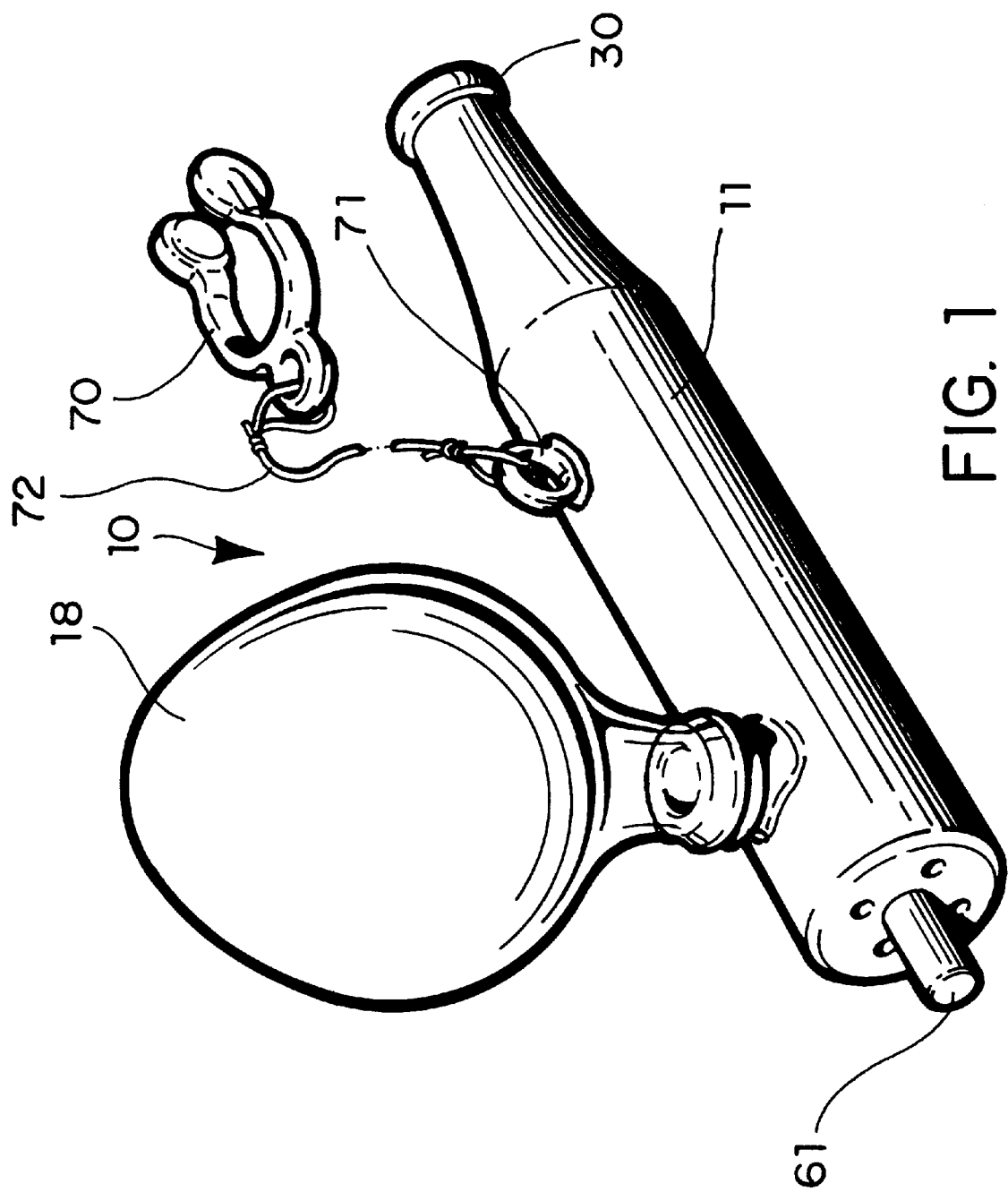
FIG. 1 is an elevated perspective view of one embodiment of the present invention comprising all preferred attachments.

The present invention is directed to a device and method for assisting in the inflation of the middle ear to equalize the pressure therein. Referring now to the figures, the present invention includes a device generally indicated at (10) comprising a body (11) having an outer surface (12) and an inner surface (13), wherein the inner surface defines a passageway (14) (see FIGS. 3–5, for example). The body also has a mouth portion (30) which is further provided with an air intake orifice (31) through which the user blows air into the passageway (14) of the body (11) upon insertion of the mouth portion (30) into the user's mouth (not shown).

Present within the passageway (14) is a valve (40) movablely disposed therein and an inner collar (43) disposed within the inner surface (13) of the body to divide the passageway (14) into two separate compartments (15, 16), as illustrated in FIGS. 3–5 and 7. For ease of explanation, the valve (40) is referred herein as the "inflation" valve, for when air is blown into the body through the air intake orifice (31) and into the first compartment (15), the "inflation" valve (40) is moved in the direction of arrow F, thereby opening the valve to allow the air to pass through and into the second compartment (16) to fill the second compartment and "inflate" the body and any receptacles attached thereto (as discussed further below). While the figures illustrate a preferred inflation valve assembly, discussed below in greater detail, it is contemplated that other suitable valve assemblies may be employed to provide the same function, namely to divide the inner passageway into separate compartments at a resting state, and to open and allow air to move from one compartment to the other as air is actively blown into the body by the user. Preferably, any one-way valve assembly commonly known by those of ordinary skill in the art may be employed to serve this function.

Figure 3:
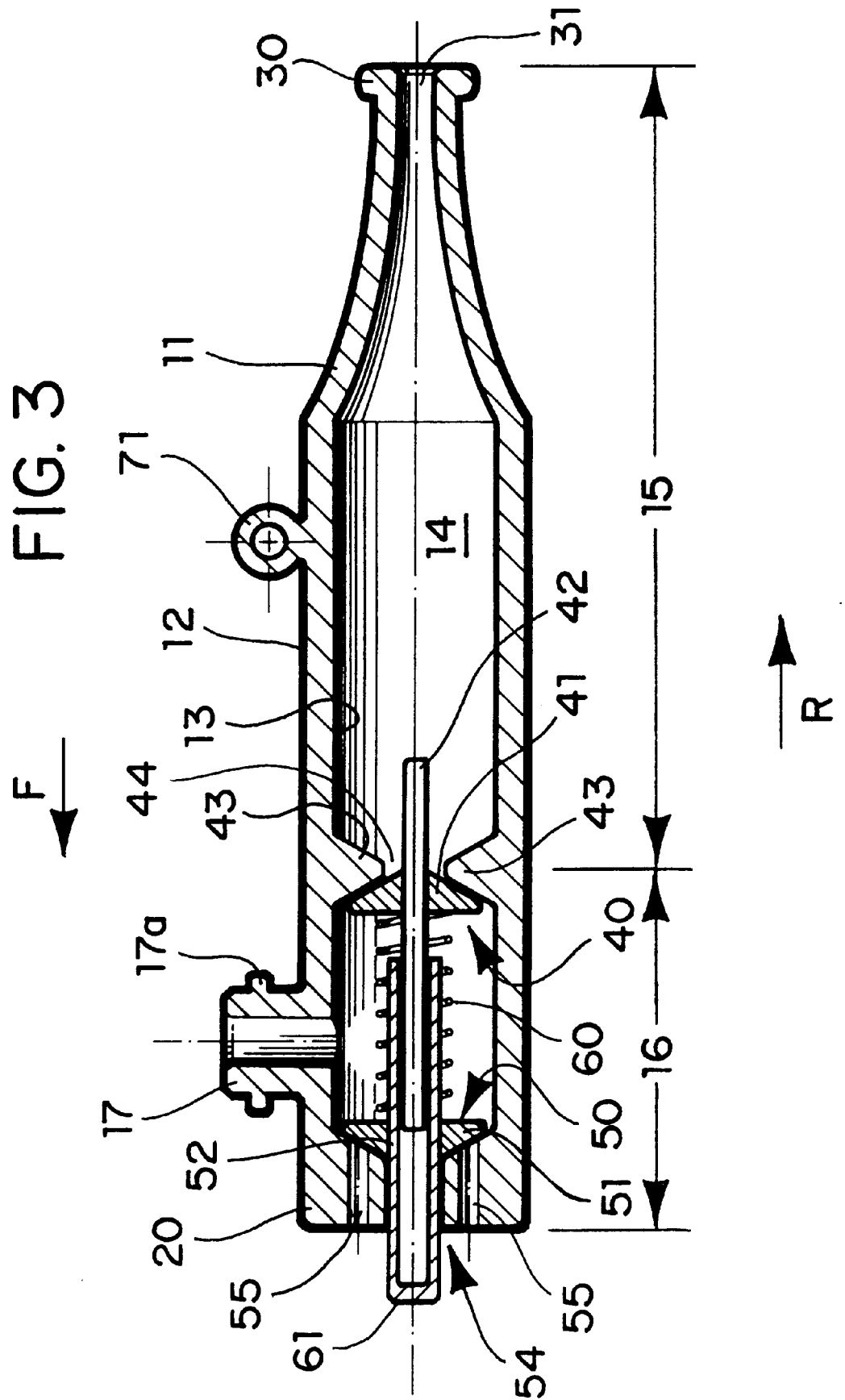
FIG. 3 is a longitudinal section taken along lines 3—3 of FIG. 2 and illustrating both valves in a closed state.
Figure 4:
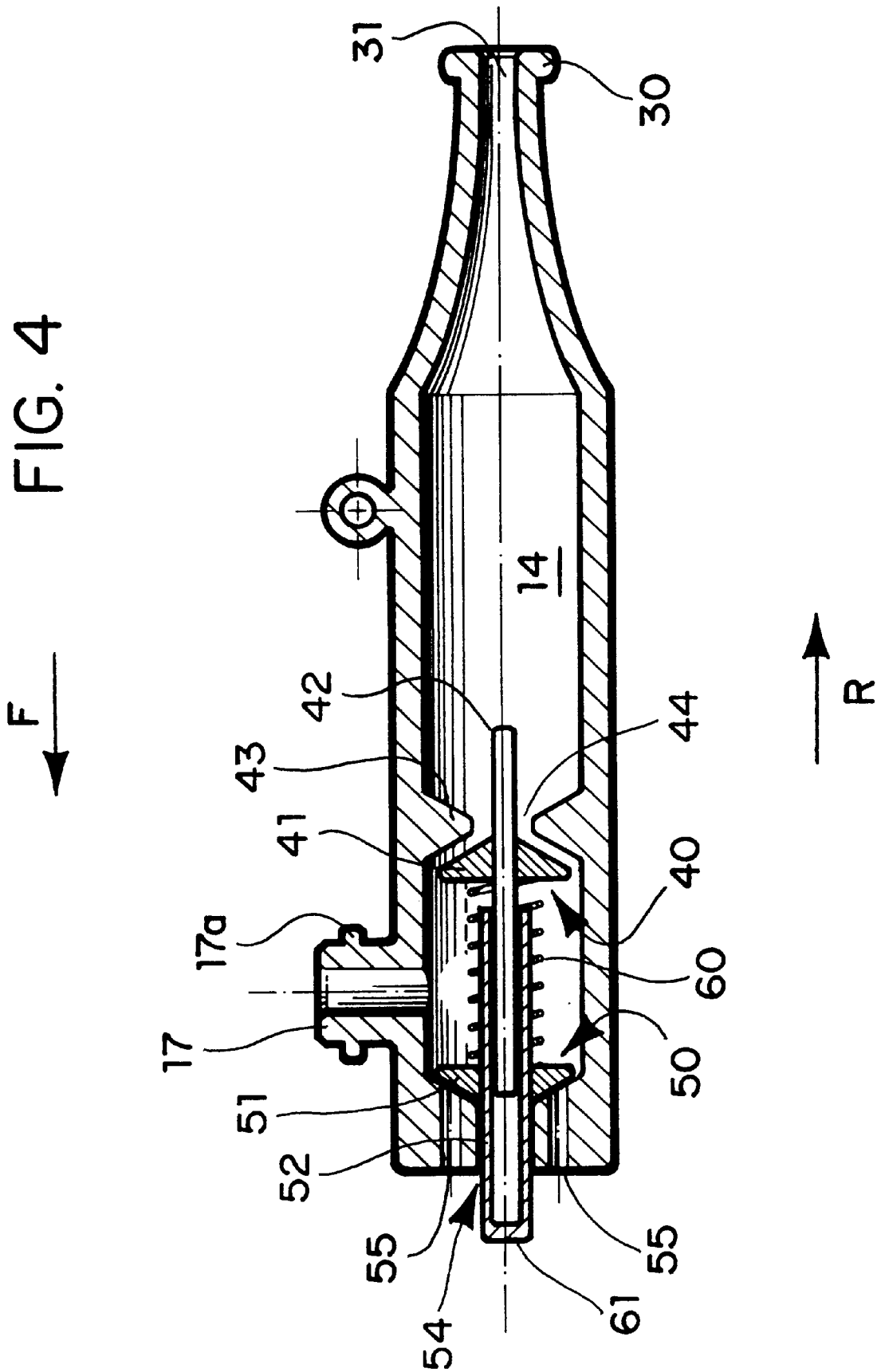
FIG. 4 is a longitudinal section similar to FIG. 3, but illustrating the inflation valve in an opened state.
Figure 5:
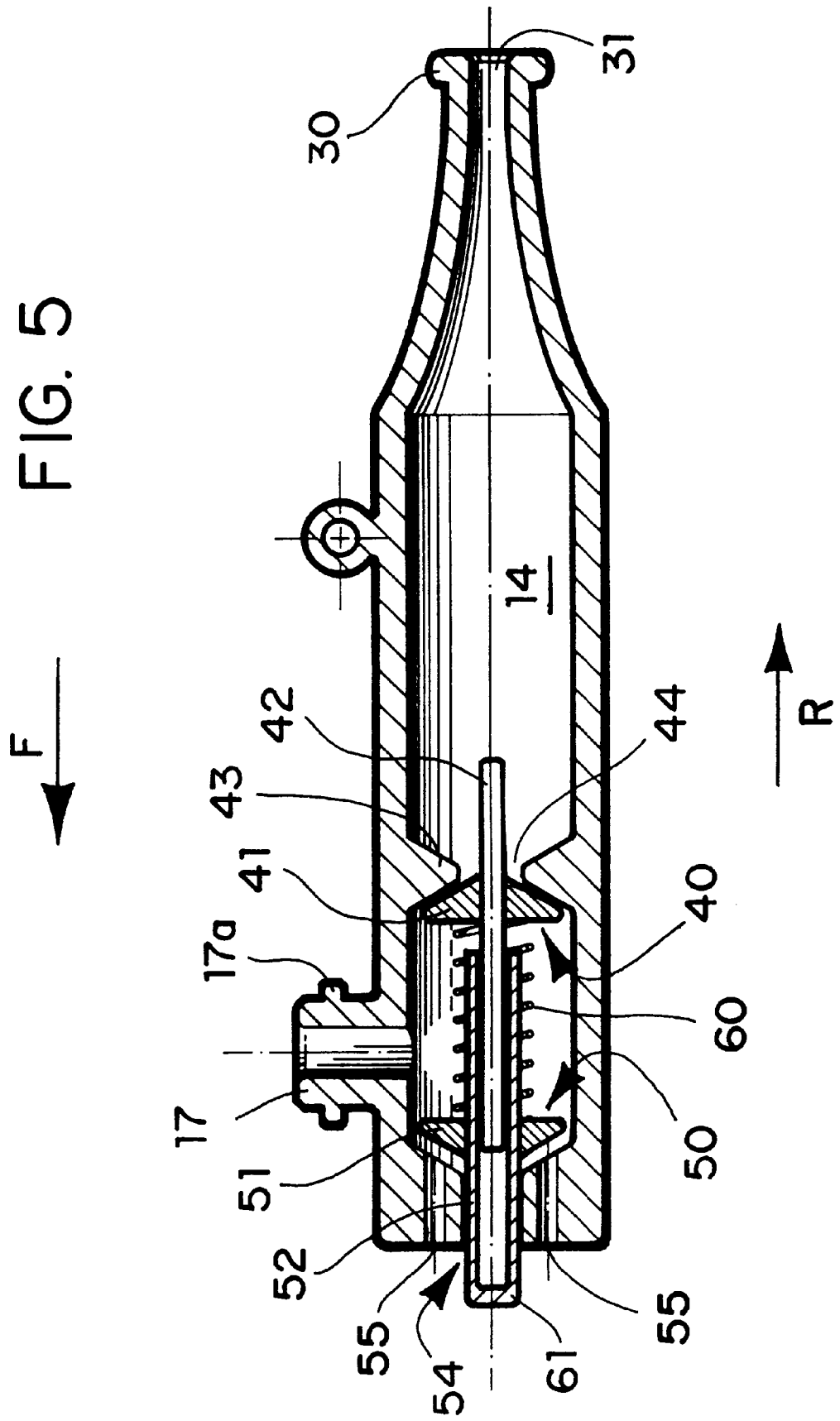
FIG. 5 is a longitudinal section similar to FIGS. 3 and 4, but illustrating the deflation valve in an opened state.
Figure 6:
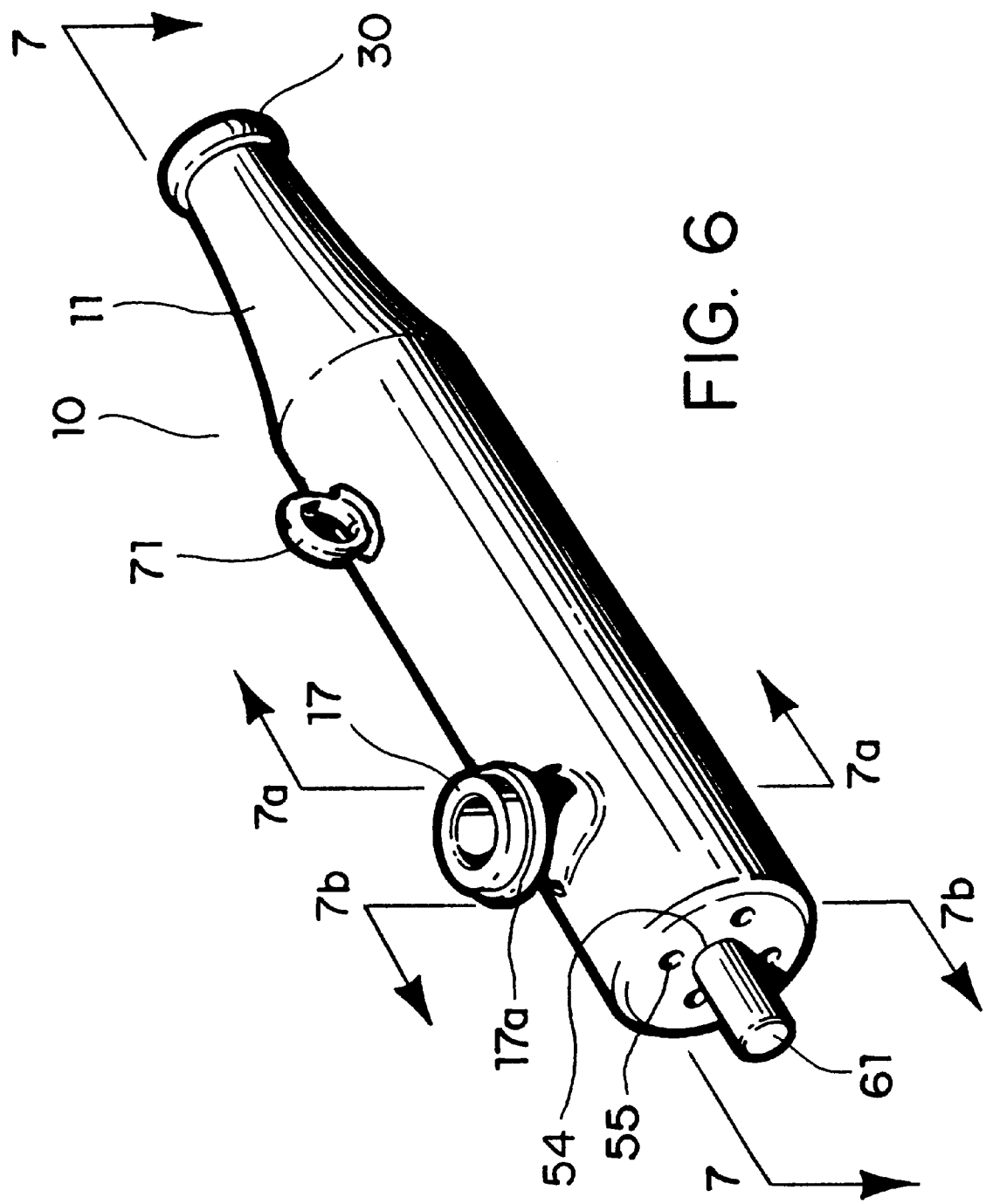

As illustrated in FIGS. 3–7 and 7A–7B, a preferred inflation valve (40) has a head portion (41) and a shaft (42) integral with the head portion. Preferably, an inner collar (43) is secured to the inner surface of the body and includes a centrally positioned orifice (44) (see FIGS. 4–7 and 7A, for example) communicating between the two compartments and configured to receive the valve head portion (41) to form a seal therein. FIGS. 3 and 5, for example, illustrate the inflation valve in a closed or resting state. The valve shaft (41) is preferably spring-biased to provide for the one-way operation of the valve as discussed above, having secured to the base of the head portion (41) a helical spring (60). While the valve shaft (42) and spring (60) may be positioned as shown in the figures, namely in combination with a second valve (i.e. "deflation" valve), as discussed further below, the opposite end of the spring not attached to the valve head portion (41) may be directly secured to the back end (20) of the body directly opposite the mouth portion (not shown). As the user blows air into the device in the direction of arrow F, the inflation valve (40) moves away from the collar (43) in the same direction by compressing the spring (60) against the second valve (or back (20) end of the body) to allow the air to enter the second compartment (16), as illustrated in FIG. 4, for example. In between user breaths, the inflation valve (40) returns to a closed or resting state to occlude the collar orifice (44), thereby preventing the movement of the air back into the first compartment.

Most preferably, the inventive device includes a second valve (50) as shown in the figures positioned within the second compartment (16) of the body. For ease of explanation, the second valve is referred herein as the "deflation" valve since it functions to release air from the second compartment, thereby "deflating" the compartment as well as any receptacles attached thereto (as discussed in further detail below). Like the inflation valve discussed above, various types of valve assemblies may be employed that are commonly known by those of ordinary skill in the art. When used in combination with the inflation valve design discussed above, a preferred deflation valve (50) comprises a head portion (51) secured to a shaft (52). The deflation valve head portion (51) is configured to occlude an air outflow port (54) communicating between the inner and outer surfaces (12, 13) of the body and with the second compartment (16) (FIG. 7B). As more clearly shown in FIGS. 3–5, for example, the shaft (52) of the deflation valve contains an inner chamber of sufficient diameter to receive the shaft (42) of the inflation valve. The deflation valve is also spring loaded via attachment to the helical spring (60). As shown in the figures, the combination of shafts (42, 52) is housed within the helical spring (60), with one end of the spring being secured to the inflation valve head portion (41) and the opposite end of the spring being secured to the deflation valve head portion (51). [For ease of viewing, the spring (60) is not shown in cross-section in the overall cross-section views illustrated in FIGS. 3–5 and 7.]

When the device is in a resting state, as shown in FIG. 3, for example, the inflation valve head portion (41) is seated within the inner collar (43), and the deflation valve head portion (51) is seated within the air outflow port (54). When air is blown into the passageway in the direction of arrow F, the inflation valve is moved away from the inner collar (43) by compressing the spring (60) against the deflation valve head portion (51). In between breaths, the inflation valve head portion (41) returns to the inner collar (43) in the direction of arrow R to occlude the orifice (44) and prevent the re-entry of the inflating air back into the first compartment (15).

Preferably, the shaft (52) of the deflation valve extends through the valve portion (51) and air outflow port (54) to operate as a lever (61) which is used to actuate or open the deflation valve. Specifically, when the user pushes the lever (61) in the direction of arrow R, the deflation valve head portion (51) is simultaneously pushed away from the air outflow port (54) in the same direction by compressing the coil (60), thereby allowing the air to exit the device through the port (54). As illustrated in FIG. 7, for example, as the user blows air into the body to open the inflation valve, the deflation valve can also be opened to allow the air to be expelled completely through the body to facilitate cleaning. In addition to the air outflow port (54), the back end (20) of the body may be provided with vents (55), as shown in the figures, to allow for a faster deflation of air from the device. Finally, when an expandable receptacle is employed, as discussed further below, the actuation of the deflation valve also allows for the deflation of the receptacle. It should be noted, however, that while a deflation valve as described and illustrated herein is preferred, a single hole in communication with the second compartment may be employed along with a simple means to open and close the hole when desired.

For best results, it is important that both valve assemblies be designed such that an airtight seal is formed when the valve is in a closed or resting state within the inner collar and air outflow port. In the embodiments illustrated herein, this is achieved by sizing the valve head portion (e.g. 41, 51) to fit snugly within the inner collar or port (e.g. 43, 54) as well as by providing an outer sealant coating to the valve head portion and/or collar. Conversely, there is no airtight seal formed between the deflation valve lever (61) and the air outflow port (54), thus allowing the air to exit the device through the air outflow port upon actuation of the deflation valve (50), as discussed above.

The inventive device (10) may further include an outer resistance port (17) having an outer annular rim (17a) to which a receptacle (18), preferably formed of an elastomeric material such as rubber or latex, for example, is attached. The rim (17a) allows for the permanent attachment of the receptacle (18) to the body and is particularly desireable for use in children where latex balloons may be employed, but if detached from the body, could result in a safety hazard to the child if ingested or inhaled. As air is blown into the second compartment (16) through the inflation valve, as discussed above, the air further moves into the receptacle (18). To deflate or remove air from the receptacle, the deflation valve may be actuated, as discussed above. One purpose of the receptacle (18) is to serve as an incentive for children to blow into the device. For this purpose, a balloon as illustrated in the figures, for example, is desirable, although the receptacle could also be formed of plastic in the shape of a toy, for example. Alternatively, the receptacle may employ an instrument for measuring the force or driving an incentive toy while exerting a retrograde force. For convenience and safety, it is important that the receptacle clear the user's face.

For optimal results in equalizing pressure in the middle ear, a receptacle formed of an elastomeric material, such as a balloon which is capable of expanding beyond its original volume, is most preferred since the combination balloon and inflation valve provide a simple means of progressively increasing the pressure required to move and open the valve (40) by adding continuous back pressure against the user as the user blows air into the body. This has the effect of more effectively sustaining pressure within the nasopharynx and is particularly advantageous in children. For example, the first portion of the tidal volume (TV) blown out against the receptacle is utilized to inflate the receptacle, which for children is typically a significant percentage of their total TV. If a child needs, for example, 40 to 60 ml of air to inflate the balloon before a back pressure is exerted, this volume may represent 30–40% of a 15-kg child's TV. The ability to generate pressure diminishes dramatically once the lungs begin to deflate. Employment of a valve assembly (such as the inflation valve described above) decreases this dead space to about 10 ml, thereby increasing the pressure to the nasopharynx immediately. While the figures illustrate one position of the inflation valve within the body, the inflation valve may be positioned anywhere within the passageway. Notably, however, the closer the inflation valve is positioned toward the user's mouth, the greater the reduction in dead space. It will also be appreciated by those of ordinary skill in the art that the resistance of the device can be varied by employing different receptacle configurations and material elasticity, or by providing different designs for incentive and measuring devices.

For the inventive device to operate effectively, the nostrils must be occluded, preferably by sealing the nares anteriorly. A nose clip (70) as illustrated in the figures, for example, is preferably employed, whereby the clip is secured anteriorly on the user's nose (not shown) to occlude the nostrils prior to use. The nose clip is particularly desirable for children who may have difficulty closing their nostrils with their fingers while simultaneously blowing air into the body of the device. To prevent loss of the nose clip, it may be secured to the body by means of a tether (72) tied to a ring (71), for example, as shown in FIG. 1. Once the nose clip (70) is attached to the user's nose, the user places the mouth portion (30) of the body in his/her mouth and blows air into the body. As the air moves through the inflation valve to inflate the receptacle as described above, an increasing and continuous back pressure is created against the user to sustain pressure within the nasopharynx to push air back up though the Eustachian tube to inflate the middle ear, thereby resulting in pressure equalization therein.

Figure 8:
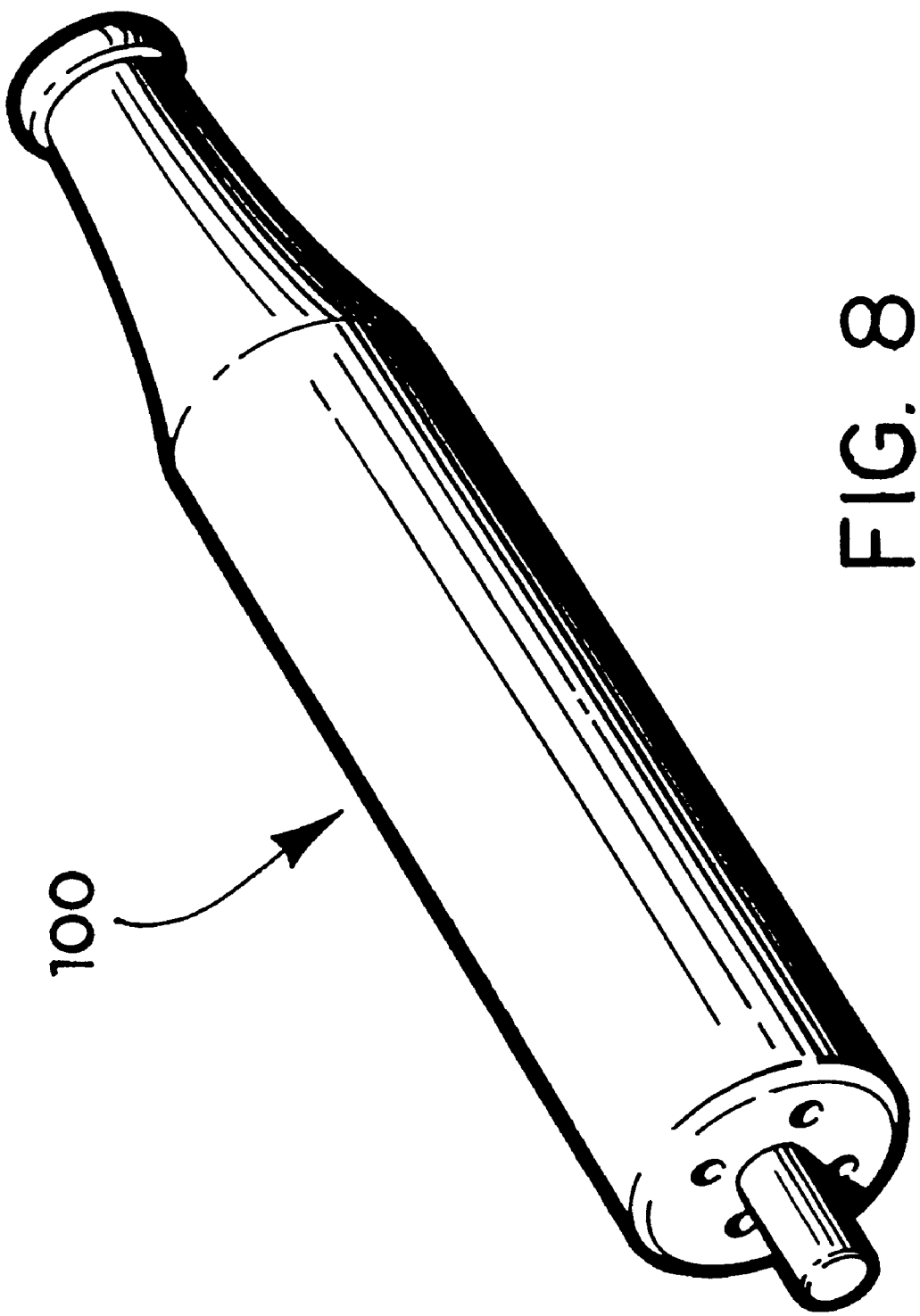
FIG. 8 is a perspective view of a second embodiment of the present invention.

As described and illustrated herein, the design of the present invention provides a simple and effective means for equalizing the pressure within the middle ear using self-generated natural air pressure and without necessitating the use of any nasal canula. FIG. 1 illustrates the most preferred embodiment (10), which includes the additional features of the separate receptacle (18) and nose clip (70), as described in detail herein. However, a second embodiment of the device (100) as illustrated in FIG. 8 may be fabricated without these latter attachments, if desired. The body of the inventive device may be manufactured of any suitable material, but most preferably a light weight, inexpensive plastic. Similarly, the valve assemblies may be formed of any suitable material commonly used in valve manufacture. Furthermore, it is contemplated that different size devices for children and adults may be employed.

The foregoing disclosure and description of the invention are illustrative and explanatory thereof, and various changes in the size, shape, and materials, as well as in the details of the illustrated construction, may be made without departing from the spirit of the invention. It is thus contemplated that one of ordinary skill in the art, having the benefit of this invention's teachings and suggestions, may employ alternate arrangements and configurations of the elements of the device, including but not limited to, the positioning of the mouth piece, the arrangement of the ports and the receptacle about the second compartment, as well as the overall shape of the body. Moreover, as discussed above, the types and positioning of the valves employed may be varied, provided that at least two separate compartments are created, with the mouth portion/air intake orifice portion being in communication with one compartment, and the receptacle, if present, being in communication with a separate compartment.

We claim:

1. A device suitable for assisting a human user in the inflation of the user's middle ear through the Eustachian tube, said device comprising:
    a body having a mouth portion and outer and inner surfaces, said inner surface defining a passageway communicating with an air intake orifice disposed within said mouth portion, wherein said mouth portion is suitable for insertion into a user's mouth for blowing air into said passageway of said body;
    a valve movably disposed within said passageway of said body to divide said passageway into adjacent first and second compartments, wherein said first compartment includes said air intake orifice, and wherein said valve is further adapted to form a seal between said compartments at a resting state to prevent air from moving between said compartments; whereby when air is blown by said user into the body through the air intake orifice, said valve is moved to an open position to allow passage of said air into said second compartment; and
    a nose clip adapted for attachment to said user's nose to occlude the user's nose during use of said device.

2. The device of claim 1, wherein said nose clip is movably secured to said device.

3. The device of claim 1, wherein said body further includes (a) a resistance port communicating through said outer and inner surfaces of the body into the second compartment and (b) a receptacle attached to said resistance port;
whereby when air is blown by said user through said air intake orifice into said second compartment, said air moves through said resistance port and into said receptacle attached thereto.

4. The device of claim 3, wherein said receptacle is formed of an elastomeric material.

5. The device of claim 3, wherein said receptacle is formed of a plastic material.

6. The device of claim 3, wherein said receptacle comprises a measuring device.

7. A device suitable for assisting a human user in the inflation of a middle ear through the Eustachian tube, said device comprising:
    a body having an outer surface and an inner surface, said inner surface defining a passageway in communication with a mouth portion, said mouth portion provided with an air intake orifice and suitable for insertion into a user's mouth for blowing air into said passageway of said body;
    an inner collar disposed within said passageway to divide said passageway into first and second compartments, said collar
    provided with an orifice communicating therethrough between said compartments, wherein said first compartment includes said air intake orifice; and
    an inflation valve movably disposed within said second compartment, wherein said inflation valve is adapted to seal said collar orifice at a resting state to prevent air from moving through said collar orifice, whereby when air is blown by said user into said body through said air intake orifice, said valve is moved away from said collar orifice to allow passage of said air into said second compartment.

8. The device of claim 7, further including a nose clip, wherein said nose clip is adapted for attachment to said user's nose to occlude the user's nostrils during use of the said device.

9. The device of claim 7, wherein said inflation valve comprises (a) a head portion adapted to be received within said collar orifice and (b) a spring-loaded shaft having sufficient compression to maintain said inflation valve head portion within said collar orifice at said resting state.

10. The device of claim 7, wherein said device further includes a deflation valve housed within said second compartment and movably disposed within said passageway to occlude an air outflow port communicating through said outer and inner surfaces of the body and into the second compartment.

11. The device of claim 7, wherein said body further includes (a) a resistance port communicating through said outer and inner surfaces of the body and into the second compartment and (b) a receptacle attached to said resistance port;
whereby when air is blown by said user through said air intake orifice and into said second compartment, said air moves through said resistance port and into said receptacle attached thereto.

12. The device of claim 11, wherein said receptacle is formed of an elastomeric material.

13. The device of claim 11, wherein said receptacle is formed of a plastic material.

14. The device of claim 11, wherein said receptacle comprises a measuring instrument.

15. A device suitable for assisting a human user in the inflation of a middle ear through the Eustachian tube, said device comprising:
    a body having an outer surface and an inner surface, said inner surface defining a passageway communicating between (a) a mouth portion provided with an air intake orifice, said mouth portion suitable for insertion into a user's mouth for blowing air into said passageway and (b) an air outflow port;

an inner collar secured to the inner surface of the body and positioned within said passageway to divide said passageway into first and second compartments, said collar further including an orifice communicating therethrough between said compartments, and wherein said first compartment includes said air intake orifice and said second compartment contains said air outflow port; and an inflation valve movably disposed within said second compartment, wherein said inflation valve is adapted to seal said collar orifice at a resting state to prevent air from moving through said collar orifice, said inflation valve further including a head portion and a shaft; whereby when air is blown by said user into said body through said air intake orifice, said inflation valve is moved away from said collar orifice to allow passage of said air into said second compartment;

a deflation valve movably disposed within said second compartment, wherein said deflation valve comprises (a) a head portion adapted to occlude said air outflow port and (b) a spring-loaded shaft having sufficient compression to maintain said deflation valve head portion within said air outflow port until said deflation valve is actuated, wherein said deflation valve shaft is connected to said inflation valve shaft; and a resistance port communicating with said second compartment and a receptacle attached to said resistance port, whereby when said air is moved within said second compartment, said air moves through said resistance port and into said receptacle.

16. The device of claim 15, wherein said valve shafts are further housed within a helical spring secured to the head portions of said valves.

17. The device of claim 15, wherein said receptacle is formed of material selected from the group consisting of plastic and an elastomeric material.

18. The device of claim 15, wherein said receptacle comprises a measuring instrument.

19. The device of claim 15, wherein said device further includes a nose clip, wherein said nose clip is adapted for attachment to said user's nose to occlude the user's nostrils during use of the said device.

* * * * *

UNITED STATES PATENT AND TRADEMARK OFFICE
CERTIFICATE OF CORRECTION

PATENT NO. : 5,950,631
DATED : September 14, 1999
INVENTOR(S) : John D. Donaldson and Krista M. Donaldson Page 1 of 2

Figure 7A:
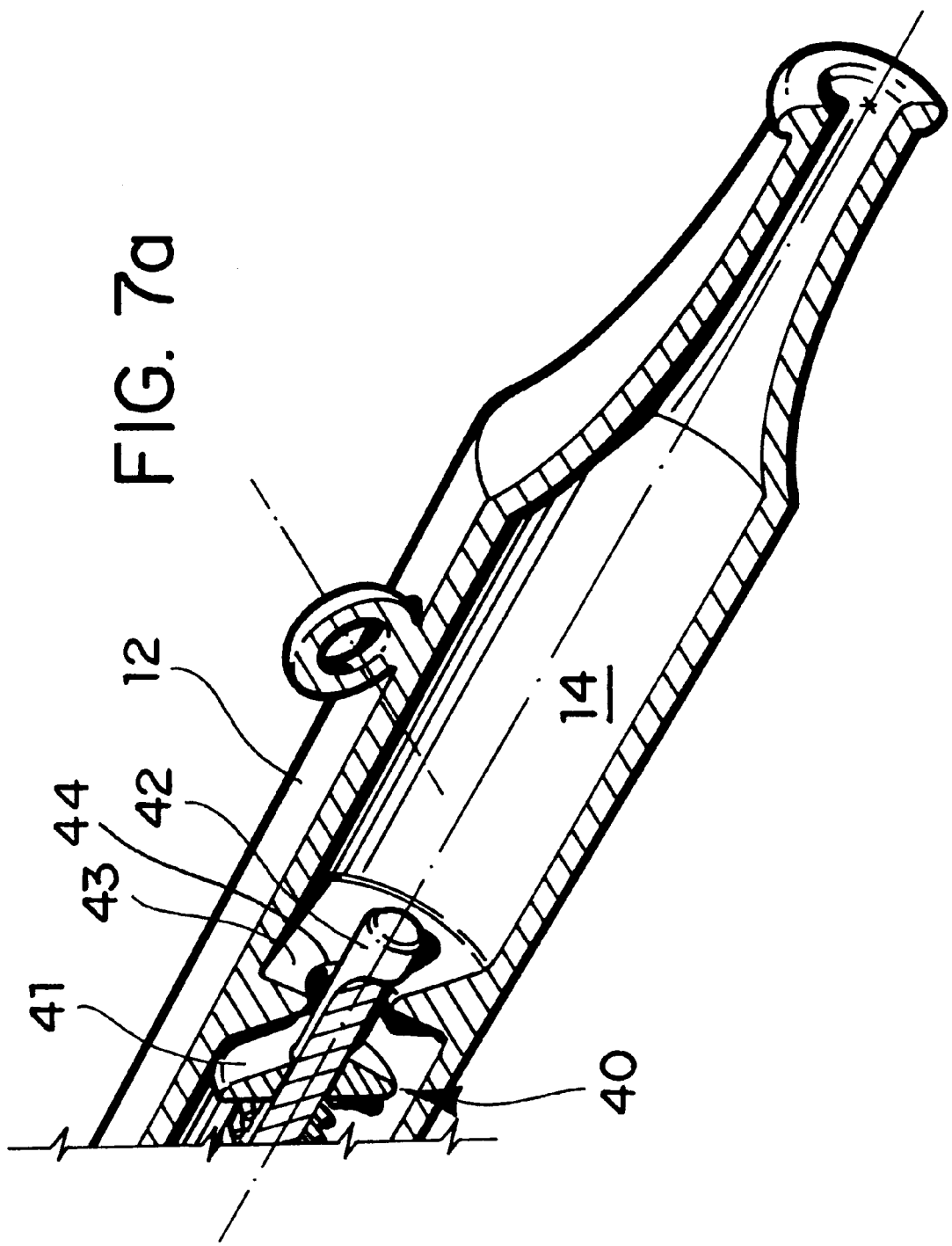
FIG. 7A is a transverse section taken along lines 7A—7A of FIG. 6 illustrating the inflation valve in an opened state.
Figure 7B:
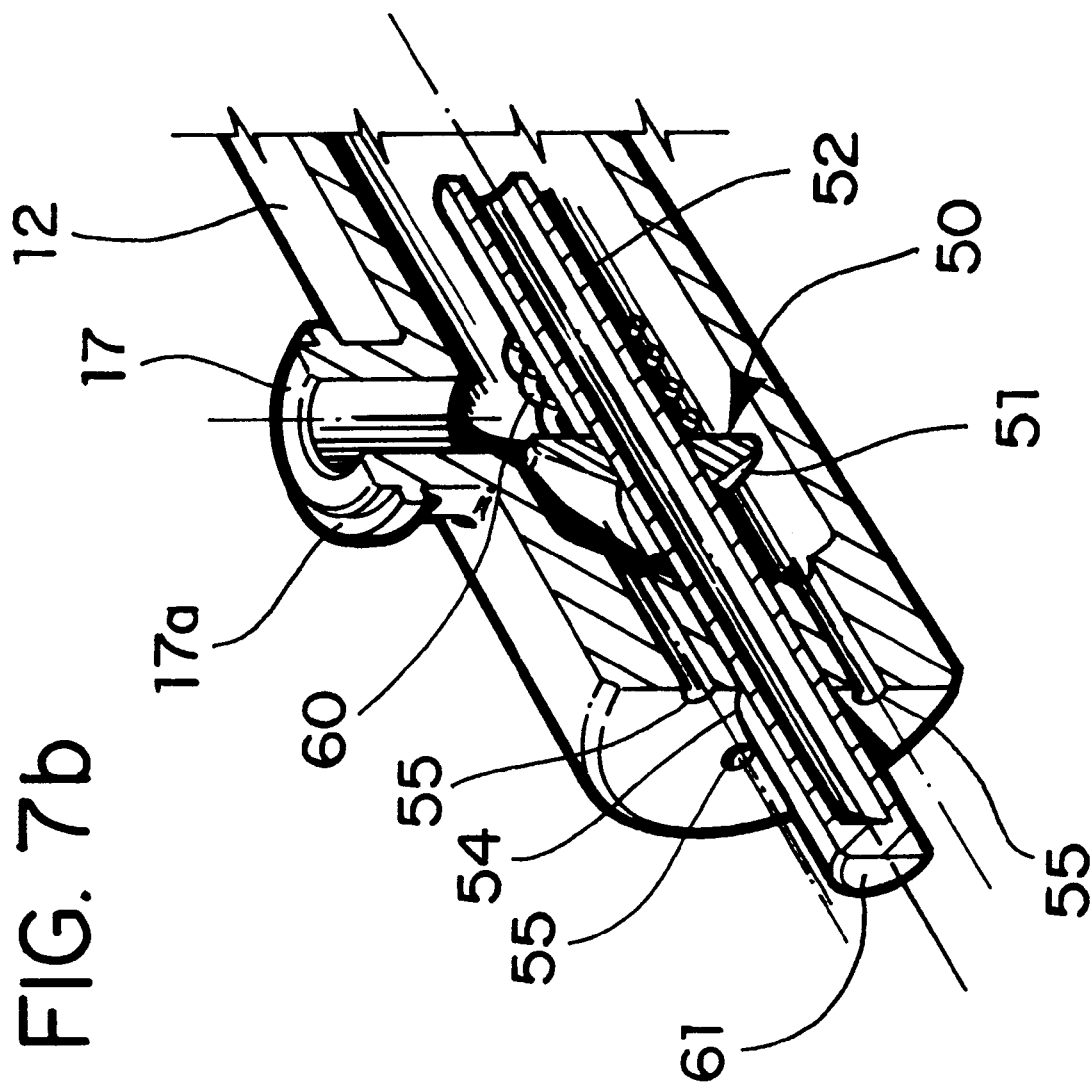
FIG. 7B is a transverse section taken along lines 7B—7B of FIG. 6 illustrating the deflation valve in an opened state.

It is certified that error appears in the above-identified patent and that said Letters Patent is hereby corrected as shown below:

On col. 3, line 55, change "FIG. 7A" to -- FIG. 7 a --; change "7A--7A" to -- 7a--7a --; and delete "transverse"

On col. 3, line 57, change "FIG. 7B" to -- FIG. 7b --; and change "7B--7B" to -- 7b--7b--; and delete "transverse"

On col. 4, line 35, change "7A" to -- 7a --.

On col. 4, line31, change "7A-7B" to --7a--7b --.

On col. 4, line 56, after "(44)" insert --(FIGS. 7 and 7a) --

UNITED STATES PATENT AND TRADEMARK OFFICE
CERTIFICATE OF CORRECTION

PATENT NO. : 5,950,631
DATED : September 14, 1999
INVENTOR(S) : John D. Donaldson and Krista M. Donaldson It is certified that error appears in the above-identified patent and that said Letters Patent is hereby corrected as shown below:

On col. 5, line 7, change "7B" to -- 7b --

On col. 5, line 16, delete "[For ease of viewing, the"
On col. 5, delete entire text on lines 17 and 18.

On col. 5, line 39, change "FIG. 7" to -- FIGS. 7 and 7b --

Figure 2:
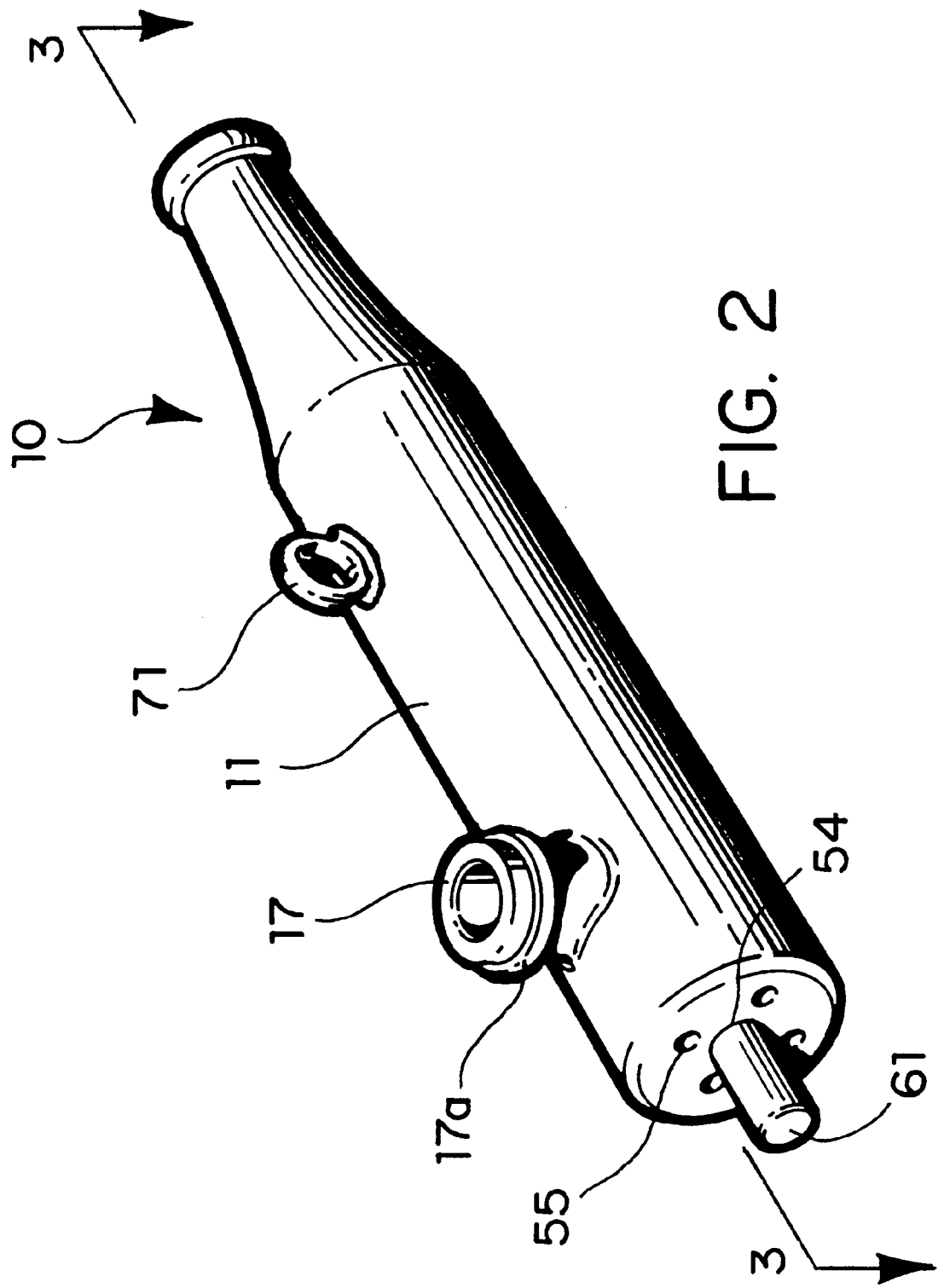
FIGS. 2 and 6 are elevated perspective views of the embodiment illustrated in FIG. 1, but without the receptacle and nose clip attachments.

On col. 6, line 2, after "attached" insert --(see FIGS. 1-3, for example) --

Signed and Sealed this

Twenty-eighth Day of November, 2000

Attest:

Q. TODD DICKINSON

*Attesting Officer*     *Director of Patents and Trademarks*